United States Patent
Kubo

(10) Patent No.: US 10,018,822 B2
(45) Date of Patent: Jul. 10, 2018

(54) LASER MICROSCOPE APPARATUS INCLUDING PHOTODETECTOR HAVING A PLURALITY OF DETECTION ELEMENTS AND AN ADJUSTING MECHANISM FOR ADJUSTING THE BEAM DIAMETER

(71) Applicant: OLYMPUS CORPORATION, Shibuya-ku, Tokyo (JP)

(72) Inventor: Hirokazu Kubo, Higashimurayama (JP)

(73) Assignee: OLYMPUS CORPORATION, Tokyo (JP)

( * ) Notice: Subject to any disclaimer, the term of this patent is extended or adjusted under 35 U.S.C. 154(b) by 54 days.

(21) Appl. No.: 14/722,519

(22) Filed: May 27, 2015

(65) Prior Publication Data

US 2015/0362715 A1    Dec. 17, 2015

(30) Foreign Application Priority Data

Jun. 11, 2014  (JP) ................................. 2014-120574

(51) Int. Cl.
*G02B 21/36* (2006.01)
*G01N 21/64* (2006.01)
(Continued)

(52) U.S. Cl.
CPC ....... *G02B 21/361* (2013.01); *G01N 21/6456* (2013.01); *G02B 21/06* (2013.01); *G02B 21/16* (2013.01); *G01N 21/6458* (2013.01)

(58) Field of Classification Search
CPC ...... G02B 21/06; G02B 21/16; G02B 21/361; G02B 21/02; G02B 21/0052;
(Continued)

(56) References Cited

U.S. PATENT DOCUMENTS 5,216,658 A * 6/1993 Clark ................... G11B 7/0055
                                                    369/100
5,596,411 A * 1/1997 Fanton ................. G01N 21/211
                                                    356/328
(Continued)

FOREIGN PATENT DOCUMENTS

JP       08062039 A    3/1996
JP    2001012902 A    1/2001
(Continued)

OTHER PUBLICATIONS

Tokuko Haraguchi, et al., "Lectures and Practice. Fluorescence Imaging of Living Cells", Osaka University & Hokkaido University, Microscope Course Book, Kyoritsu Shuppan Co., Ltd., pp. 150 & 151.

(Continued)

*Primary Examiner* — Thanh Luu
*Assistant Examiner* — Jennifer Bennett
(74) *Attorney, Agent, or Firm* — Holtz, Holtz & Volek PC

(57) ABSTRACT

By using a PPD as a detector, photon count loss is reduced to the utmost, and the incident light-intensity range in which light can be detected is widened. Provided is a laser microscope apparatus including an objective lens that collects return light from a specimen; a collimator lens that converts the return light collected by the objective lens into a substantially collimated beam, a PPD including a plurality of pixels that detect the return light converted to a substantially collimated beam by the collimator lens; and a controller that makes the beam diameter of the return light incident on the PPD substantially equal to an effective detection area of the PPD, formed by the plurality of pixels.

20 Claims, 7 Drawing Sheets

(51) Int. Cl.
*G02B 21/06* (2006.01)
*G02B 21/16* (2006.01)

(58) Field of Classification Search
CPC ... G01N 2021/6478; G01N 2201/6038; G01N 21/6458; G01N 21/6456; G01N 2021/6463
USPC ........ 250/201.1, 216, 559.04, 559.05, 201.2, 250/201.3, 221; 359/379, 368, 382, 383; 348/79
See application file for complete search history.

(56) References Cited

U.S. PATENT DOCUMENTS

| | | | | |
|---|---|---|---|---|
| 6,028,306 | A * | 2/2000 | Hayashi | G02B 21/0032 |
| | | | | 250/235 |
| 7,304,790 | B2 | 12/2007 | Kawano et al. | |
| 7,952,722 | B2 * | 5/2011 | Chan | A61B 3/102 |
| | | | | 356/492 |
| 2002/0043611 | A1 | 4/2002 | Yoshikawa et al. | |
| 2007/0114362 | A1 * | 5/2007 | Feng | G01N 21/6428 |
| | | | | 250/208.1 |
| 2008/0055718 | A1 | 3/2008 | Kono et al. | |
| 2008/0158566 | A1 * | 7/2008 | Suzuki | G02B 13/22 |
| | | | | 356/450 |
| 2008/0261242 | A1 * | 10/2008 | Goix | G01N 21/6428 |
| | | | | 435/7.21 |
| 2008/0266551 | A1 | 10/2008 | Araki et al. | |
| 2010/0067102 | A1 | 3/2010 | Yokoi et al. | |
| 2011/0043619 | A1 | 2/2011 | Wolleschensky | |
| 2012/0162754 | A1 | 6/2012 | Liedtke et al. | |
| 2012/0206590 | A1 | 8/2012 | Yamamoto et al. | |
| 2012/0228802 | A1 * | 9/2012 | Kan | B29C 67/0066 |
| | | | | 264/401 |
| 2012/0320184 | A1 | 12/2012 | Seyfried et al. | |
| 2013/0128268 | A1 | 5/2013 | Tomioka | |
| 2015/0008309 | A1 | 1/2015 | Wolleschensky et al. | |
| 2016/0169806 | A1 | 6/2016 | Dantus et al. | |
| 2016/0169937 | A1 | 6/2016 | Labuda et al. | |
| 2016/0231547 | A1 | 8/2016 | Kubo | |
| 2017/0184834 | A1 | 6/2017 | Wolleschensky et al. | |

FOREIGN PATENT DOCUMENTS

| | | | | |
|---|---|---|---|---|
| JP | 2008275763 | A | 11/2008 | |
| JP | 2010091694 | A | 4/2010 | |
| JP | 2011082298 | A | 4/2011 | |
| JP | 2012133368 | A * | 7/2012 | ........... G02B 21/006 |
| JP | 2013003587 | A | 1/2013 | |
| JP | 2015515018 | A | 5/2015 | |
| WO | 2010134351 | A1 | 11/2010 | |

OTHER PUBLICATIONS

"Lecture and Practice, Live-cell fluorescence imaging, Osaka University and Hokkaido University, Microscopy course book", edited by Tokuko Haraguchi, et al., Kyoritsu Shuppan Co., Ltd., pp. 151 and 152.
U.S. Appl. No. 15/008,249; Title: "Laser Microscope Apparatus"; First Named Inventor: Hirokazu KUBO; Date Filed: Jan. 27, 2016.
Japanese Office Action (and English translation thereof) dated Dec. 19, 2017, issued in counterpart Japanese Application No. 2014-120574.

* cited by examiner

LASER MICROSCOPE APPARATUS INCLUDING PHOTODETECTOR HAVING A PLURALITY OF DETECTION ELEMENTS AND AN ADJUSTING MECHANISM FOR ADJUSTING THE BEAM DIAMETER

TECHNICAL FIELD

This application is based on Japanese Patent Application No. 2014-120574, the contents of which are incorporated herein by reference.

The present invention relates to a laser microscope apparatus.

BACKGROUND ART

In the related art, there are known laser microscope apparatuses that use PMTs (photomultiplier tubes) as detectors (for example, see Non Patent Literature 1). In addition to PMTs, other known types of detectors are PPDs (Pixelated Photon Detectors, multipixel photon detectors), such as MPPCs (Multi-Pixel Photon Counters), SiPMs (Silicon Photomultipliers), and multipixel avalanche photodiodes.

When detecting light, if a PPD is used in an operating mode in which a constant-intensity signal is output regardless of the intensity of the light, that is to say, a Geiger mode, it is possible to detect ultraweak light at the level of a single photon. In addition, in the case where a PPD is used in the Geiger mode, the number of photons that can be detected per unit time is on the order of 1 photon per pixel; however, since a PPD is a multipixel device, even if a large number of photons is incident on the PPD, it is possible to detect the number of photons corresponding thereto. In other words, a PPD can widen incident light-intensity range.

CITATION LIST

Non Patent Literature

{NPL 1}
Tokuko HARAGUCHI, Hiroshi KIMURA, Yasushi HIRAOKA, Eds., "Lectures and Practice. Fluorescence Imaging of Living Cells. Osaka University/Hokkaido University, Microscope Course Book", Kyoritsu Shuppan Co., Ltd., p150-151

SUMMARY OF INVENTION

Technical Problem

In the case where comparatively strong light is incident on a PPD, if the photons are not evenly distributed to each pixel, photon count loss occurs due to the response speed limitation of the device itself.

The present invention provides a laser microscope apparatus that uses a PPD as a detector and in which photon count loss is reduced to the utmost so as to enable detection of light ranging from weak light to intense light with high sensitivity.

Solution to Problem

A first aspect of the present invention is a laser microscope apparatus including an objective lens that collects light from a specimen; a photodetector including a plurality of detection elements that detect the light collected by the objective lens; and an adjusting mechanism that makes a beam diameter of the light incident on the photodetector substantially equal to an effective detection area of the photodetector formed by the plurality of detection elements.

With the above-described aspect of the present invention, the light from the specimen which is collected by the objective lens is detected by the plurality of detection elements in the photodetector. Even when the number of photons that can be detected per unit time by each detection element is assumed to be the single-photon level, by detecting photons with the plurality of detection elements, it is possible to widen the light-intensity incidence range in which light from the specimen can be detected.

In this case, by making the beam diameter of the light substantially equal to the effective detection area of the photodetector by means of the adjusting mechanism, it is easy to make the photons in the light from the specimen uniformly incident on each detection element. Therefore, photon count loss is reduced to the utmost, and it is possible to further widen the light-intensity incident range in which the light from the specimen can be detected.

In the above-described aspect, the adjusting mechanism may adjust the beam diameter according to an exit NA of the objective lens.

When the exit NA of the objective lens changes, the beam diameter of the light incident on the photodetector also changes. With this configuration, even in the case where the objective lens to be use is changed, the beam diameter of the light and the effective detection area of the photodetector can be made substantially uniform by means of the adjusting mechanism. Accordingly, it is possible to prevent photon count loss caused by changing the objective lens.

In the above-described aspect, the adjusting mechanism may include a collimator lens that converts the light collected by the objective lens into a substantially collimated beam; and a controller that moves the collimator lens to a prescribed position in an optical-axis direction, which is determined in advance according to the exit NA of the objective lens.

With this configuration, since the beam diameter of the light at the photodetector can be changed according to the position of the collimator lens in the optical-axis direction, by means of the controller, it is possible to adjust the light to an appropriate beam diameter that fills the effective detection area of the photodetector, according to the objective lens being used.

In the above-described aspect, the adjusting mechanism may include a collimator lens group formed of a plurality of groups of optical systems that convert the light collected by the objective lens into a substantially collimated beam; and a controller that moves at least one of the groups of optical systems to a prescribed position in the optical-axis direction, which is determined in advance according to the exit NA of the objective lens.

With this configuration, it is possible to reduce the movement range of each optical system compared with a case in which a collimator lens formed of a single-group optical system is used. In addition, it is possible to more precisely convert the light incident on the photodetector to a collimated beam compared with a collimator lens formed of a single-group optical system, which makes it possible to reduce detection loss of the light caused by an angular dependency.

The above-described aspect may further include a switching mechanism that can switch among a plurality of the collimator lens groups, which have different spacings between the optical systems in the optical-axis direction, wherein the controller may switch to the collimator lens group which is determined in advance according to the exit NA of the objective lens.

With this configuration, it is possible to easily make the beam diameter of the light substantially equal to the effective detection area of the photodetector simply by switching among each collimator lens group according to the objective lens being used, without having to adjust the position of each optical system in the optical-axis direction.

In the above-described aspect, the adjusting mechanism may further include a collimator lens that converts the light collected by the objective lens into a substantially collimated beam; a uniform-illumination element that is disposed, so as to be capable of moving in the optical-axis direction, between the collimator lens and the photodetector, and that causes the light converted to a substantially collimated beam by the collimator lens to diverge to form a substantially uniform intensity distribution; and a controller that moves the uniform-illumination element to a prescribed position in the optical-axis direction, which is determined in advance according to the exit NA of the objective lens.

With this configuration, the beam diameter of the light when it is diverged differs according to the position of the uniform-illumination element in the optical-axis direction. In this case, the light that is made to diverge by the uniform-illumination element has a uniform intensity distribution, and thereby it is possible to shape the beam to an appropriate beam diameter that fills the effective detection area of the photodetector with a uniform intensity distribution, as well as to further reduce photon count loss, simply by using the controller to move the uniform-illumination element to a prescribed position according to the objective lens being used.

In the above-described aspect, the prescribed position may be determined in consideration of a wavelength dependency for the exit NA of the objective lens.

With this configuration, it is possible to move the collimator lens or the uniform-illumination element to the optimum position in the optical-axis direction to shape the beam to an appropriate beam diameter, regardless of the wavelength dependency of the exit NA for each objective lens.

In the above-described aspect, the adjusting mechanism may include a collimator lens that converts the light collected by the objective lens to a substantially collimated beam; a diverging element that causes the light converted to a substantially collimated beam by the collimator lens to diverge; and an internal-surface reflection element that reflects the light diverged by the diverging element at an internal surface thereof to converge inside the effective detection area of the photodetector.

With this configuration, after the light which will be incident on the photodetector has been temporarily diverged by the diverging element, it is reflected by the internal-surface reflection element at the internal surface thereof and converges inside the effective detection area of the photodetector. Therefore, the return light can be made to converge on substantially the entire surface of the effective detection area of the photodetector, which allows a reduction in photon count loss to be achieved.

The above-described aspect may further include a detecting apparatus in which a plurality of the photodetectors are arranged in an array in directions intersecting the optical axis; wherein, so as to make the beam diameter of the light incident on the detecting apparatus substantially equal to the effective detection area of the detecting apparatus, formed by the plurality of photodetectors, the adjusting mechanism may switch the photodetectors to be driven according to the beam diameter of the light.

With this configuration, the effective detection area of the detecting apparatus can be made substantially equal to the beam diameter of the light, and thus, the photons can be easily made uniformly incident on each detection element of the plurality of photodetectors. In this case, photodetector outside of the beam diameter of the light incident on the detection elements do not need to be driven. Therefore, only the required photodetectors are driven by the adjusting mechanism, and thus dark noise can be reduced.

In the above-described aspect, the adjusting mechanism may drive the photodetectors which are determined in advance according to the exit NA of the objective lens.

With this configuration, it is possible to easily make the effective detection area of the detecting apparatus substantially equal to the beam diameter of the light, according to the objective lens being used.

In the above-described aspect, the photodetector may be formed in such a manner that the sizes of the detection elements become smaller the closer the detection elements are disposed to a center portion of the effective detection area of the detecting apparatus, and is formed in such a manner that the sizes of the detection elements become larger the closer the detection elements are disposed to edge portions of the effective detection area of the detecting apparatus.

The photon density of the light incident on the detecting apparatus differs between the optical axis center and edges, and photons tend to concentrate at positions closer to the optical axis center. Therefore, with this configuration, photons that concentrate at the optical-axis center can be losslessly detected, and it is thus possible to reduce photon count loss.

In the above-described aspect, the detection elements may output constant-intensity signals regardless of the intensity of the detected light.

With this configuration, it is possible to detect ultraweak light at the single-photon level with high precision.

Advantageous Effects of Invention

The present invention affords an advantage in that, using a PPD as a detector, it is possible to widen the incident light-intensity range in which light can be detected while avoiding photon count loss.

DESCRIPTION OF EMBODIMENTS

First Embodiment

A laser microscope apparatus according to a first embodiment of the present invention will be described below with reference to the drawings.

Figure 1:
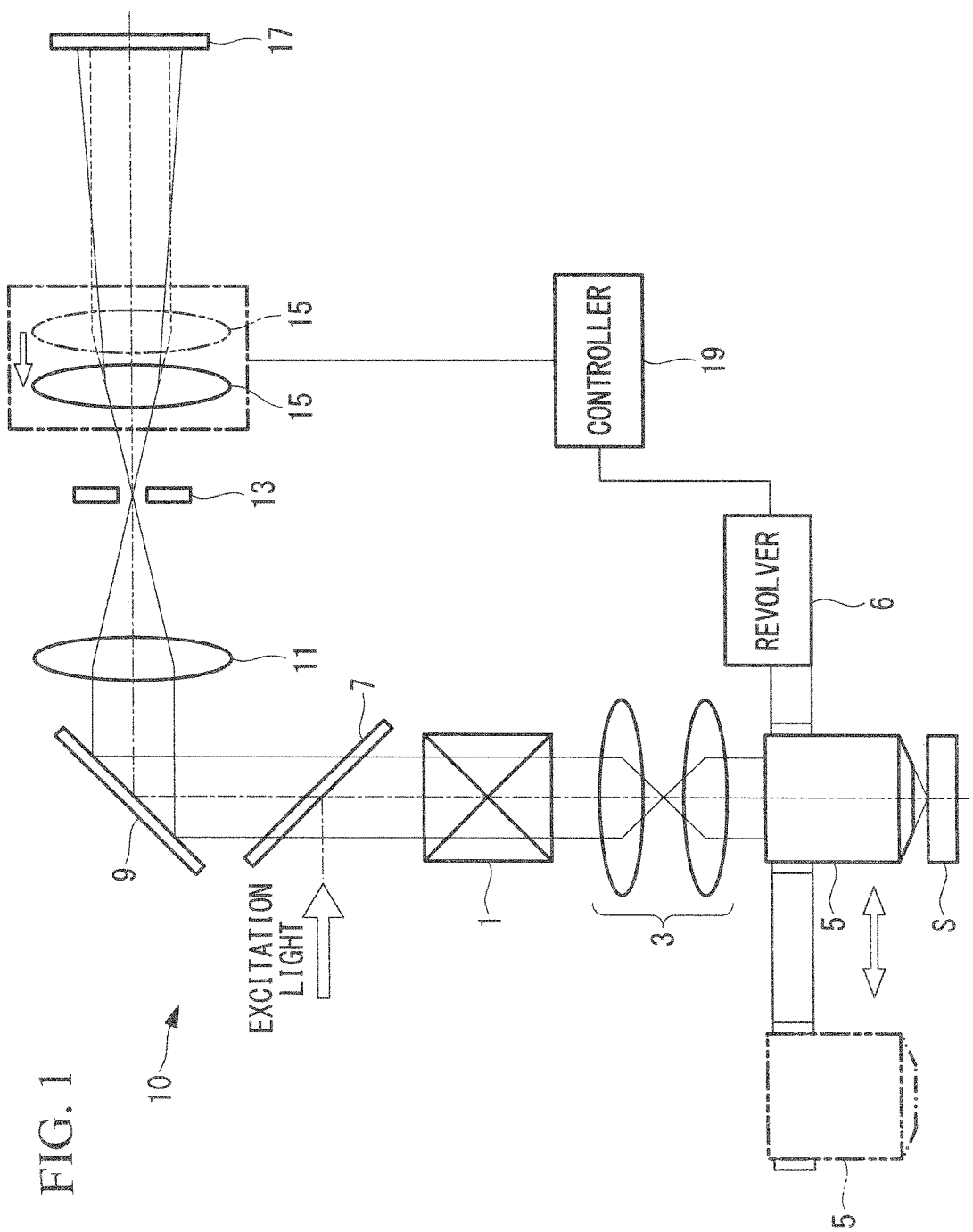
FIG. 1 is a diagram showing, in outline, the configuration of a laser microscope apparatus according to a first embodiment of the present invention.

As shown in FIG. 1, a laser microscope apparatus 10 according to this embodiment includes a light source (not illustrated) that generates excitation light, an XY galvanometer mirror 1 that two-dimensionally scans the excitation light emitted from the light source, a relay optical system 3 that relays the excitation light scanned by the XY galvanometer mirror 1, and an objective lens 5 that radiates the excitation light relayed by the relay optical system 3 onto a specimen S and that collects return light (for example, fluorescence) emitted from the specimen S.

In addition, the laser microscope apparatus 10 includes a dichroic mirror 7 that splits off the return light collected by the objective lens 5 and returning along the light path of the excitation light, a reflecting mirror 9 that reflects the split-off return light, a focusing lens 11 that focuses the return light reflected by the reflecting mirror 9, a confocal aperture 13 that restricts the passage of the focused return light, a collimator lens (adjusting mechanism) 15 that converts the return light that has passed through the confocal aperture 13 to a substantially collimated beam, a PPD (Pixelated Photon Detector, photodetector) 17 that detects the light converted to a substantially collimated beam by the collimator lens 15, and a controller (adjusting mechanism) 19 that performs adjustment or the like of the position of the collimator lens 15 in the optical-axis direction.

The objective lens 5 is supported by a revolver 6 together with other objective lenses 5.

The revolver 6 is configured so as to be capable of selectively inserting any one of the objective lenses 5 into the light path of the excitation light, under the control of the controller 19 or by a manual operation, and switching the objective lens 5 that is inserted into the light path of the excitation light.

The dichroic mirror 7 is configured to reflect the excitation light coming from the light source towards the XY galvanometer mirror 1 and to transmit the return light returning from the specimen S along the light path of the excitation light via the objective lens 5, the XY galvanometer mirror 1, etc. towards the reflecting mirror 9.

The confocal aperture 13 is disposed at a position that is optically conjugate with the specimen S and is configured to allow only light from the focal position of the objective lens 5 to pass therethrough.

The PPD 17 is, for example, an MPPC (Multi-Pixel Photon Counter), an SiPM (Silicon Photomultiplier), a multi-pixel avalanche photodiode, or the like. This PPD 17 has a plurality of pixels (detecting elements, not illustrated) that detect the return light. The detecting elements are the units that perform photon detection.

Each pixel is configured to detect photons in the return light and output a pulse. Thus, the PPD 17 outputs the sum of the outputs of the individual pixels as an intensity signal. The PPD 17 is set to be driven in the Geiger mode, in which each pixel outputs a pulse of constant intensity regardless of the incident light intensity. When the PPD 17 is driven in the Geiger mode, the number of photons that each pixel detects per unit time is on the order of a single photon.

The controller 19 stores the position of the collimator lens 15 in the optical-axis direction, which is determined in advance according to the exit NA of the objective lens 5 so that the beam diameter of the return light incident on the PPD 17 and the effective detection area of the PPD 17 formed by the plurality of pixels are made substantially equal. The beam diameter of the light incident on the PPD 17 is determined by exit pupil diameter×projection magnification of the objective lens 5 when the return light is collimated to form a collimated beam and is incident on the PPD 17; however, by adjusting the position of the collimator lens 15, it is possible to convert the beam to a noncollimated beam and to adjust the diameter of the beam incident on the PPD 17. According to the objective lens 5 that is used, this controller 19 moves the collimator lens 15 to a prescribed position in the optical-axis direction, which is stored in association with that objective lens 5.

Figure 2:
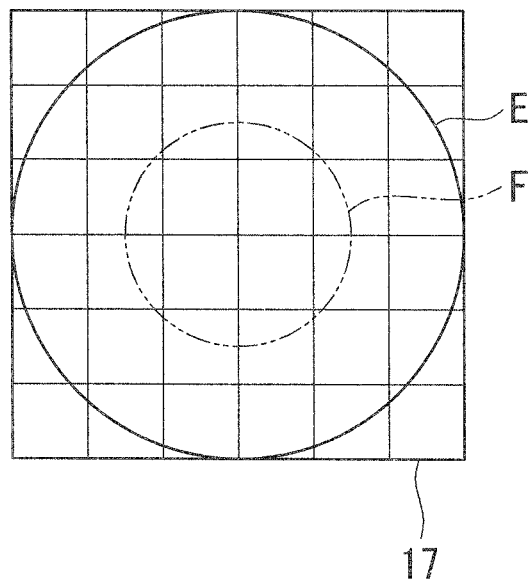
FIG. 2 is a diagram showing the beam diameter of return light at the position of a PPD in FIG. 1.

For example, when an objective lens 5 having a small exit NA is used, the beam diameter of the return light after passing through the confocal aperture 13 becomes small. Therefore, the controller 19 moves the collimator lens 15 in the direction away from the PPD 17. Accordingly, the exit beam from the collimator lens 15 diverges slightly, and the beam diameter of the return light at the position of the PPD 17 is expanded to be made substantially equal to the effective detection area of the PPD 17, like the beam E shown by the solid-line circle in FIG. 2. The beam F shown by the dotted-line circle in FIG. 2 represents the beam diameter of the return light before performing position adjustment of the collimator lens 15, in the case where the objective lens 5 having the small exit NA is used.

On the other hand, when an objective lens 5 having a large exit NA is used, the beam diameter of the return light after passing through the confocal aperture 13 becomes large. Therefore, the controller 19 moves the collimator lens 15 in the direction in which it approaches the PPD 17. Accordingly, the exit beam from the collimator lens 15 becomes a collimated beam or a slightly converging beam, and the beam diameter of the return light at the position of the PPD 17 is made substantially equal to the effective detection area of the PPD 17, like the beam E shown in FIG. 2.

In addition, when the insertion/switching of the objective lens 5 is electrically controlled, the controller 19 performs the position adjustment of the collimator lens 15 on the basis of switching information for the objective lens 5. When the insertion/switching of the objective lens 5 is performed manually, the controller 19 performs the position adjustment of the collimator lens 15 on the basis of information about the objective lens 5 currently being used, which the user inputs. A sensor that senses the type of objective lens 5 being used and that sends information thereon to the controller 19 may be provided.

The operation of the thus-configured laser microscope apparatus 10 will now be described.

In the case where an image of the specimen S is to be acquired with the laser microscope apparatus 10 according to this embodiment, the objective lens 5 is set up, the position of the collimator lens 15 in the optical-axis direction is adjusted by the controller 19, and the excitation light is emitted from the light source.

At this time, the controller 19 moves the collimator lens 15 to a prescribed position that is determined in advance in association with the exit NA of the objective lens 5, so that the beam diameter of the return light incident on the PPD 17 is made substantially equal to the effective detection area of the PPD 17. For example, when the exit NA of the objective lens 5 being used is small, the collimator lens 15 is moved to a position away from the PPD 17, as shown in FIG. 1.

After the excitation light emitted from the light source is reflected by the dichroic mirror 7, it is scanned by the XY galvanometer mirror 1, is relayed by the relay optical system 3, and is radiated on the specimen S by the objective lens 5. Accordingly, the laser light is two-dimensionally scanned on the specimen S according to the oscillating movement of the XY galvanometer mirror 1.

The return light emitted from the specimen S due to irradiation with the laser light is collected by the objective lens 5, then passes through the dichroic mirror 7 via the relay optical system 3 and the XY galvanometer mirror 1, is reflected by the reflecting mirror 9, and is focused by the focusing lens 11. In the return light focused by the focusing lens 11, only light coming from the focal position of the objective lens 5 in the specimen S passes through the confocal aperture 13, is converted to a substantially collimated beam by the collimator lens 15, and is incident on the PPD 17.

At the PPD 17, the incident return light is detected by the individual pixel, which then output constant-intensity pulses, and an intensity signal which is the sum thereof is output. Accordingly, for example, in a PC (Personal Computer) or the like, which is not illustrated, it is possible to generate a two-dimensional image on the basis of the intensity signal output from the PPD 17 and scanning position information of the excitation light scanned by the XY galvanometer mirror 1.

By driving the PPD 17 in the Geiger mode, even ultraweak light at the level of single photons can be detected by each pixel. Thus, with a plurality of pixels, by detecting a photon at each of these pixels, it is possible to improve the return-light detection sensitivity and to widen the incident light-intensity range in which the return light can be detected, compared with a case such as that where the return light is detected with, for example, a PMT (photomultiplier tube).

In this case, by adjusting the position of the collimator lens 15 in the optical-axis direction using the controller 19 to make the beam diameter of the return light incident on the PPD 17 substantially equal to the effective detection area of the PPD 17, the photons in the return light from the specimen S are easily distributed to each pixel and are made uniformly incident thereon.

Also in the case where the exit NA of the objective lens 5 being used is large, by using the controller 19 to move the collimator lens 15 to a prescribed position that is associated with the exit NA of the objective lens 5 and that is determined in advance, which is a position close to the PPD 17 in this case, the beam diameter of the return light incident on the PPD 17 can be made substantially equal to the effective detection area of the PPD 17, and the photons in the return light can be easily made uniformly incident on each pixel.

Therefore, with the laser microscope apparatus 10 according to this embodiment, using the PPD 17 as a detector, and photon count loss can be reduced to the utmost, making it possible to detect light in a wider incident light-intensity range in which the return light from the specimen S can be detected.

This embodiment can be modified in the following ways.

Figure 3:
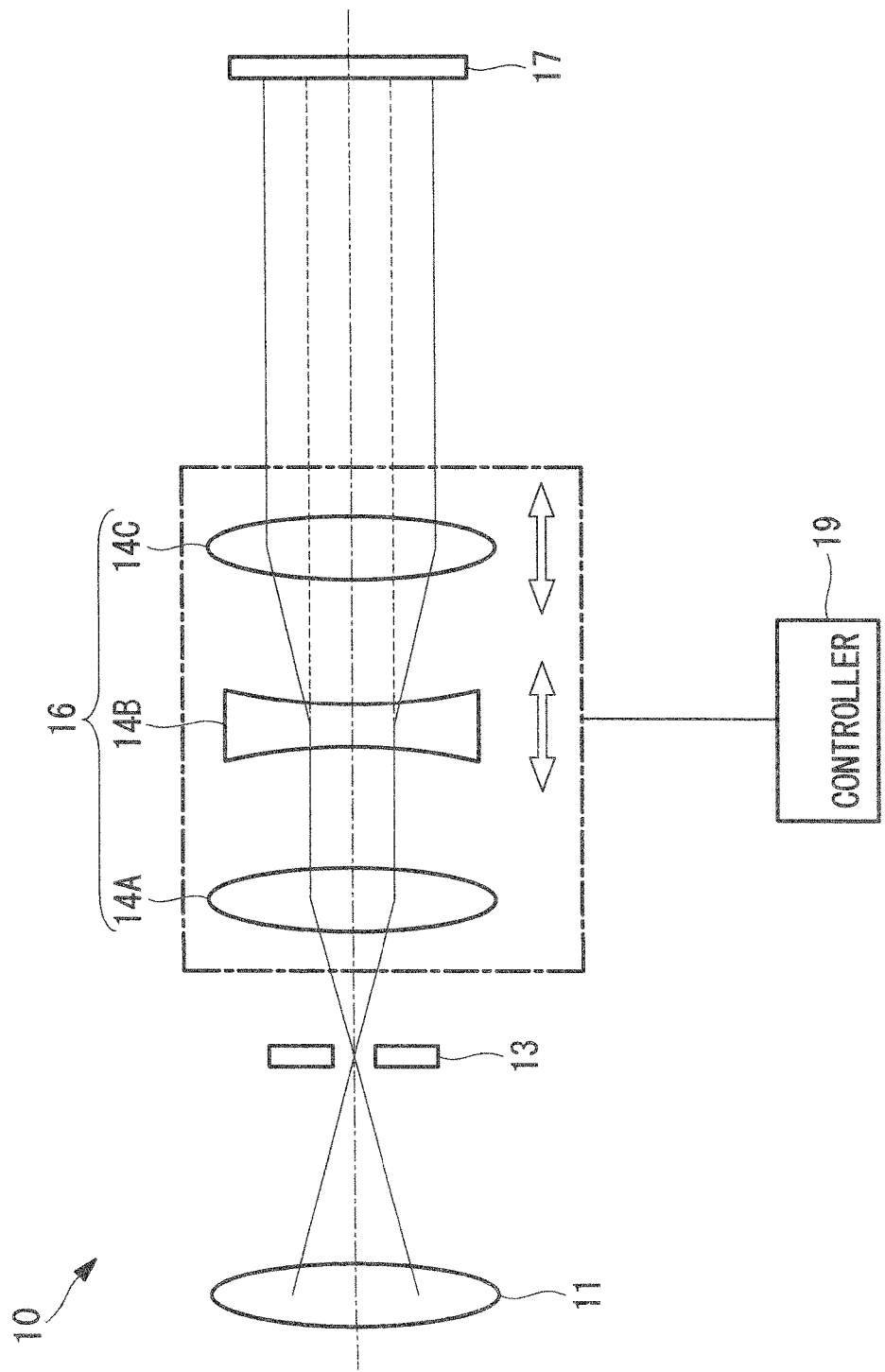
FIG. 3 is a diagram showing, in outline, the configuration of a laser microscope apparatus according to a first modification of the first embodiment of the present invention.

Although this embodiment has been described in terms of a collimator lens 15 that is formed of a single-group optical system, as a first modification, as shown in FIG. 3, a collimator lens group 16 that is formed of a plurality of groups (three groups in this modification) of optical systems 14A, 14B, and 14C may be used.

In this case, the controller 19 should move at least one group of the optical systems 14A, 14B, and 14C (for example, the two groups of optical systems 14B and 14C) to a prescribed position in the optical-axis direction, which is determined in advance according to the exit NA of the objective lens 5, thereby making the beam diameter of the incident return light substantially equal to the effective detection area of the PPD 17, formed by a plurality of pixels.

By doing so, compared with the case in which the collimator lens 15 formed of the single-group optical system is moved, it is possible to reduce the moving range of the optical systems 14A, 14B, and 14C. In addition, it is possible to convert the return light to a collimated beam with higher precision compared with the collimator lens 15 formed of a single-group optical system, and it is possible to reduce the detection loss of the return light due to angular dependency.

In this modification, for example, the collimator lens group 16 may be formed of two groups of optical systems, and the position of only one group of the optical systems may be adjusted in the optical-axis direction.

In addition, in this modification, a switching mechanism (not illustrated) that can switch among a plurality of collimator lens groups 16 having different spacings between the optical systems 14A, 14B, and 14C in the optical-axis direction may be provided, and the controller 19 may switch to a collimator lens group 16 that is determined in advance according to the exit NA of the objective lens 5 being used. In this case, combinations of the exit NAs of the objective lenses 5 and the plurality of collimator lens groups 16 which are associated so that the beam diameter of the return light incident on the PPD 17 and the effective detection area of the PPD 17 are made substantially equal should be stored in the controller 19.

By doing so, it is possible to easily make the beam diameter of the return light substantially equal to the effective detection area of the PPD 17 merely by switching the whole collimator lens group 16 to match the objective lens 5 being used, without adjusting the positions of the individual optical systems 14A, 14B, and 14C in the optical-axis direction.

Figure 4:
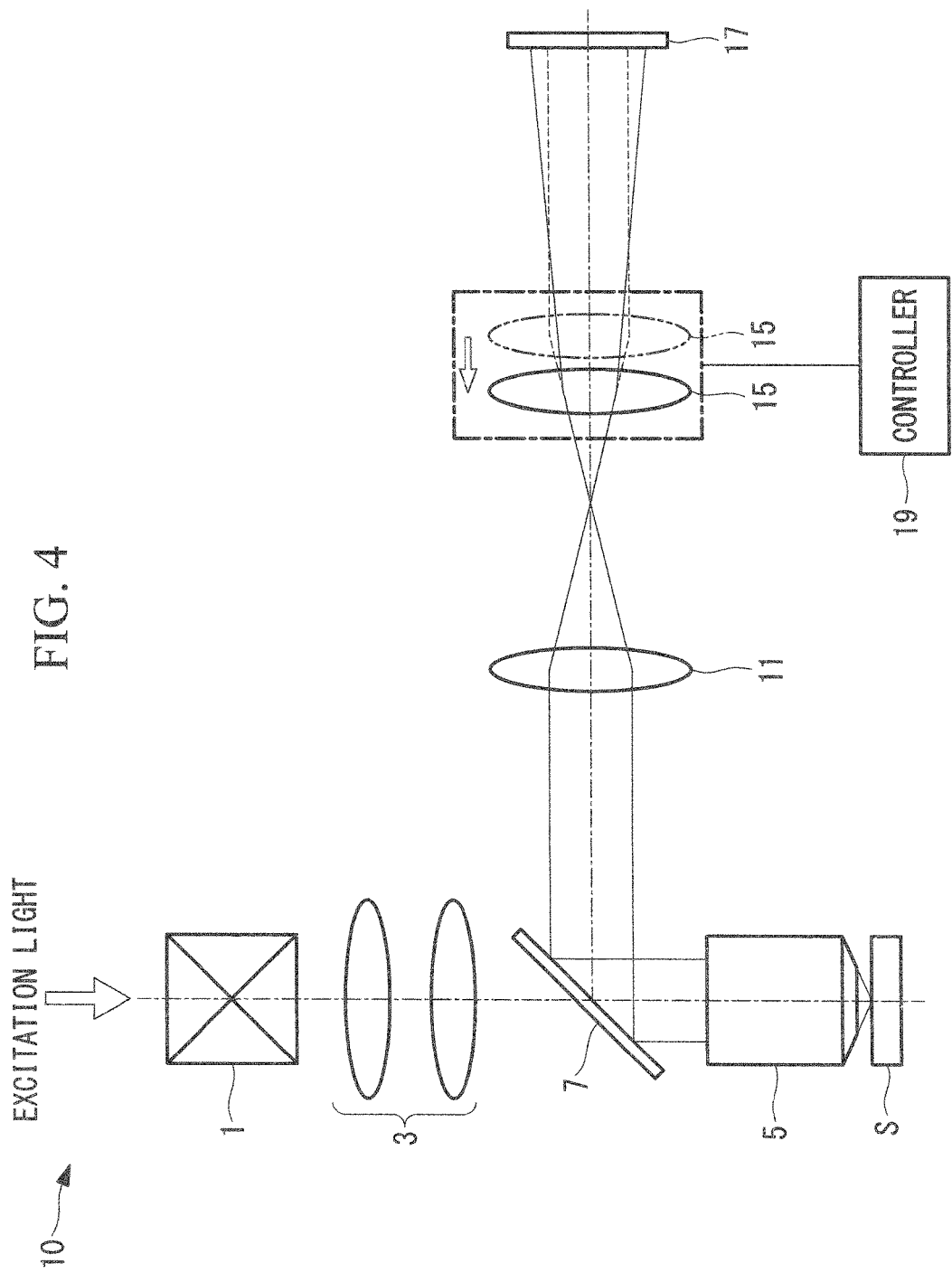
FIG. 4 is a diagram showing, in outline, the configuration of a laser microscope apparatus according to a second modification of the first embodiment of the present invention.

In this embodiment, although it has been assumed that only the light coming from the focal position of the objective lens 5 is detected using the confocal aperture 13, as a second modification, as shown in FIG. 4, an infrared pulsed laser beam that induces two-photon excitation may be used as the excitation light, and the fluorescence generated by two-photon excitation may be detected, without using the confocal aperture 13.

In this case, the return light emitted from the specimen S and collected by the objective lens 5 is split off from the light path by the dichroic mirror 7 without passing via the XY galvanometer mirror 1, and should be detected by the PPD 17 via the focusing lens 11 and the collimator lens 15.

By doing so, it is possible to observe only the focusing position of the infrared pulsed laser light in the three-dimensional space in the specimen S.

In this modification, similarly to the first modification, the collimator lens group 16 may be used instead of the collimator lens 15.

In addition, in this embodiment and these modifications, the prescribed position of the collimator lens 15 may be determined by taking into consideration the wavelength dependency at the exit NA of the objective lens 5.

By doing so, it is possible to move the collimator lens 15 to the optimum position in the optical-axis direction to form a suitable beam diameter, regardless of the wavelength dependency for the exit NA of each objective lens 5.

Second Embodiment

Next, a laser microscope apparatus according to a second embodiment of the present invention will be described.

Figure 5:
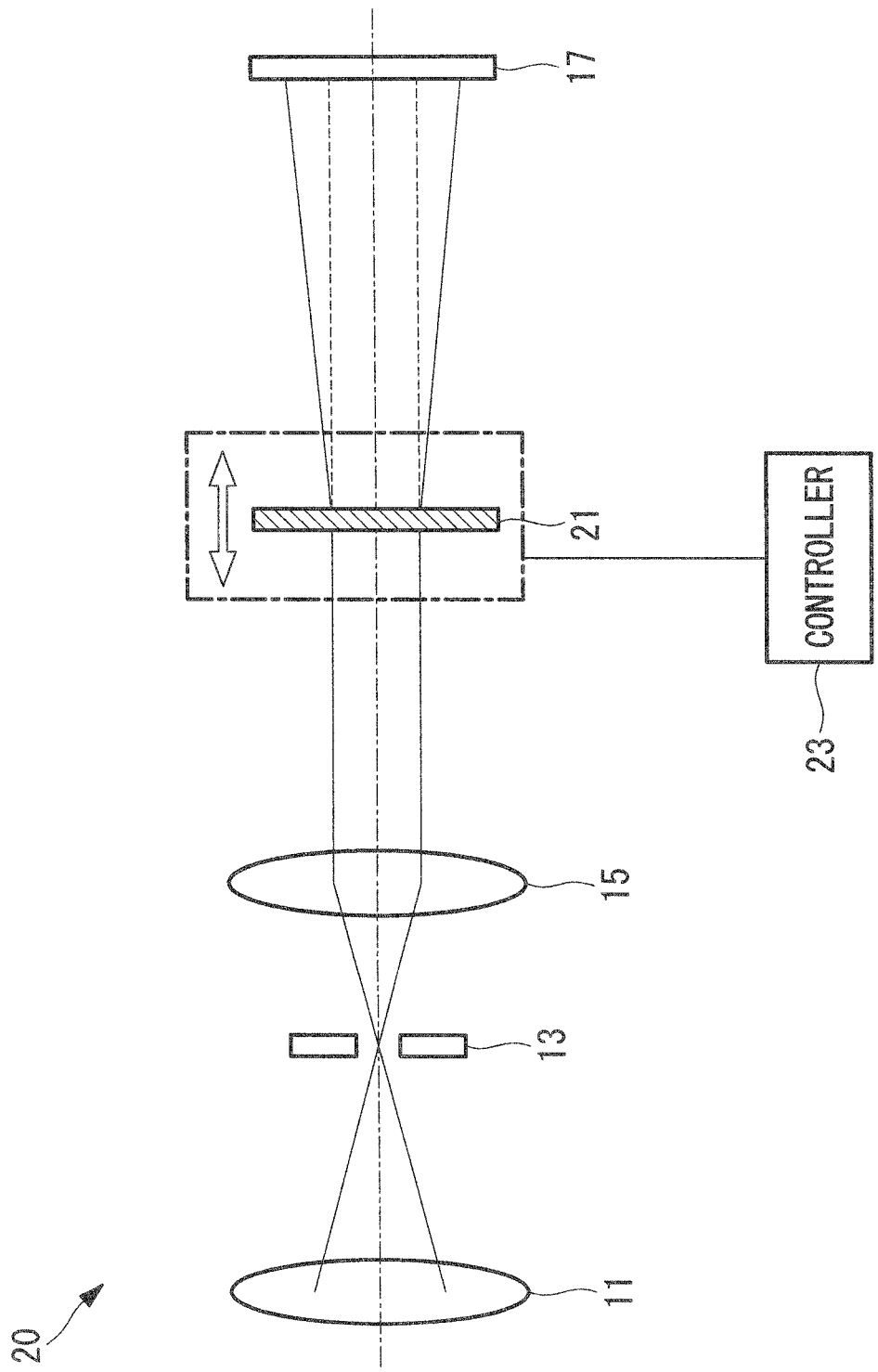
FIG. 5 is a diagram showing, in outline, the configuration of a laser microscope apparatus according to a second embodiment of the present invention.

As shown in FIG. 5, a laser microscope apparatus 20 according to this embodiment differs from the first embodiment in that it includes a uniform-illumination element (adjusting mechanism) 21 that causes the return light converted to a substantially collimated beam by the collimator lens 15 to diverge to form a substantially uniform intensity distribution, and also includes, instead of the controller 19, a controller (adjusting mechanism) 23 that controls the position of the uniform-illumination element 21 in the optical-axis direction.

In the following, parts having the same configuration as those in the laser microscope apparatus 10 according to the first embodiment are assigned the same reference signs, and a description thereof will be omitted.

Examples of the uniform-illumination element 21 include a diffusing plate, a simple lens, a fly-eye lens, a homogenizer (fly-eye lens+imaging lens), a holographic diffuser, or the like. This uniform-illumination element 21 is provided between the collimator lens 15 and the PPD 17 in such a manner as to be movable in the optical-axis direction. The beam diameter of the return light incident on the PPD 17 when it diverges changes according to the position of the uniform-illumination element 21 in the optical-axis direction.

The controller 23 stores the position of the uniform-illumination element 21 in the optical-axis direction, which is determined according to the exit NA of the objective lens 5, so as to make the beam diameter of the return light incident on the PPD 17 and the effective detection area of the PPD 17 formed by the plurality of pixels substantially equal. According to the objective lens 5 being used, this controller 23 moves the uniform-illumination element 21 to a prescribed position in the optical-axis direction, which is stored in association with the objective lens 5.

With the thus-configured laser microscope apparatus 20, for example, when using the objective lens 5 having the small exit NA, because the beam diameter of the return light after being converted to a substantially collimated beam by the collimator lens 15 is small, the uniform-illumination element 21 is moved by the controller 23 to a position farther away from the PPD 17. By increasing the distance between the uniform-illumination element 21 and the PPD 17, it is possible to increase the beam diameter of the return light incident on the PPD 17, and to make the beam diameter of the return light substantially equal to the effective detection area of the PPD 17.

On the other hand, when using the objective lens 5 having the large exit NA, because the beam diameter of the return light after being converted to a substantially collimated beam by the collimator lens 15 is large, the uniform-illumination element 21 is moved by the controller 23 to a position closer to the PPD 17. By reducing the distance between the uniform-illumination element 21 and the PPD 17, the increase in the beam diameter of the return light incident on the PPD 17 due to the divergence can be suppressed, and it is possible to make the beam diameter of the return light substantially equal to the effective detection area of the PPD 17.

In this case, by using the uniform-illumination element 21 to cause the return light from the specimen S to diverge to form a substantially uniform intensity distribution, return light having a substantially uniform intensity distribution can be made incident on the PPD 17, regardless of the beam diameter.

As described above, with the laser microscope apparatus 20 according to this embodiment, by using the controller 23 to move the uniform-illumination element 21 to a prescribed position which is determined in advance, in accordance with the objective lens 5 being used, it is possible to form a suitable beam diameter that fills the effective detection area of the PPD 17 with a uniform intensity distribution, and photon count loss can be further reduced.

In this embodiment, the prescribed position of the uniform-illumination element 21 may be determined by taking into account the wavelength dependency for the exit NA of the objective lens 5.

By doing so, it is possible to move the uniform-illumination element 21 to the optimum position in the optical-axis direction to form a suitable beam diameter, regardless of the wavelength dependency for the exit NA of each objective lens 5.

Third Embodiment

Next, a laser microscope apparatus according to a third embodiment of the present invention will be described.

Figure 6:
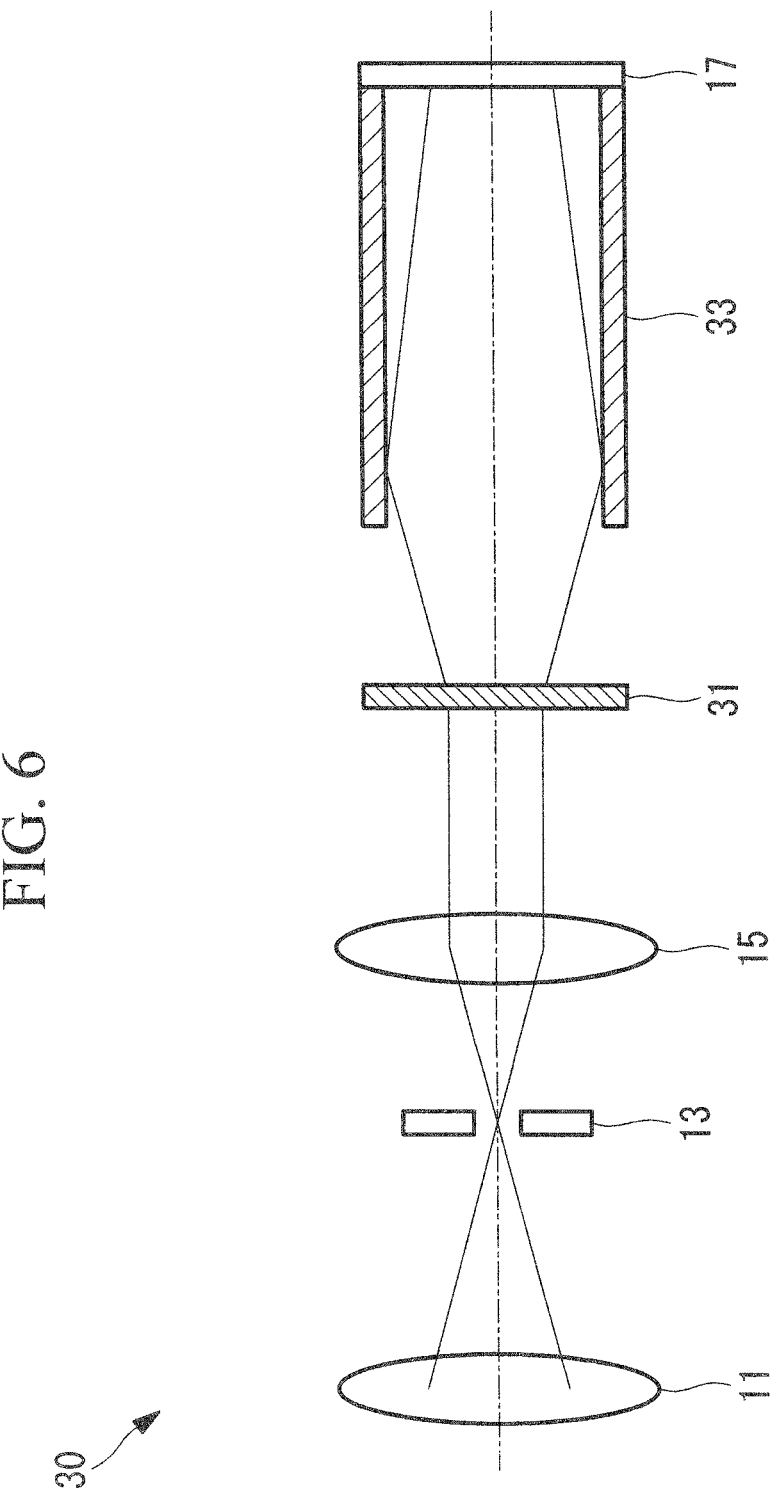
FIG. 6 is a diagram showing, in outline, the configuration of a laser microscope apparatus according to a third embodiment of the present invention.

As shown in FIG. 6, a laser microscope apparatus 30 according to this embodiment differs from the first embodiment in that it does not include the controller 19, but includes a diverging element (adjusting mechanism) 31 that causes the return light converted to a substantially collimated beam by the collimator lens 15 to diverge, and an internal-surface reflection element (adjusting mechanism) 33 that reflects the return light diverged by the diverging element 31 at an internal surface thereof and that causes it to converge inside the effective detection area of the PPD 17.

In the following, parts having the same configuration as those in the laser microscope apparatus 10 according to the first embodiment are assigned the same reference signs, and a description thereof will be omitted.

In this embodiment, the PPD 17 is assumed to have a substantially quadrangular effective detection area formed by the plurality of pixels.

As the beam diverging element 31, for example, a diffusing plate, a simple lens, a fly-eye lens, a holographic diffuser, etc. may be used.

The internal-surface reflection element 33 is, for example, formed in the shape of a quadrangular tube that is hollow in the longitudinal direction, and an opening area at the exit end thereof has substantially the same size as the effective detection area of the PPD 17. This internal-surface reflection element 33 is provided in front of the PPD 17 and is disposed so that the exit end thereof is closed off by the PPD 17. The four inner surfaces of internal-surface reflection element 33 are each formed of reflecting mirrors.

With the thus-configured laser microscope apparatus 30, the return light converted to a substantially collimated beam by the collimator lens 15 is temporarily made to diverge by the diverging element 31 and then enters the internal-surface reflection element 33 at one end thereof. The return light that enters the internal-surface reflection element 33 at one end thereof is reflected at the internal surfaces by the reflecting mirrors and exits from the other end thereof, and converges in the effective detection area of the PPD 17. At this time, the beam diameter of the light incident on the PPD 17 is formed into a substantially quadrangular shape by the internal-surface reflection element 33.

Therefore, with the laser microscope apparatus 30 according to this embodiment, the return light is made to converge on substantially the entire surface of the effective detection area of the PPD 17, and thus it is possible to achieve a reduction in photon count loss. In addition, by forming the beam diameter of the return light into a quadrangular shape with the internal-surface reflection element 33, it is possible to efficiently make the return light incident on the substantially the entire surface of the substantially quadrangular effective detection area of the PPD 17, and thus, it is possible to further reduce photon count loss.

Fourth Embodiment

Next, a laser microscope apparatus according to a fourth embodiment of the present invention will be described.

Figure 7:
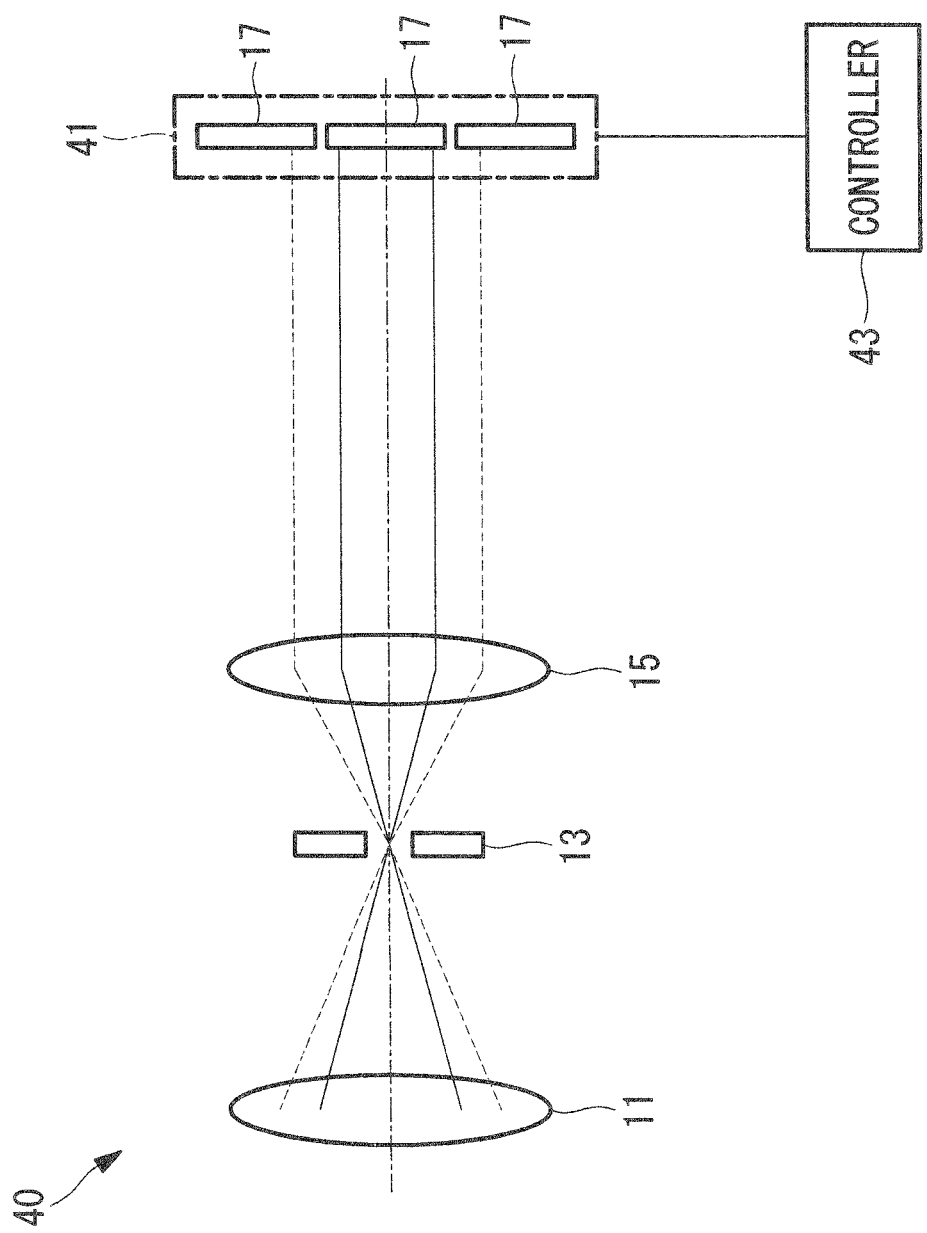
FIG. 7 is a diagram showing, in outline, the configuration of a laser microscope apparatus according to a fourth embodiment of the present invention.

As shown in FIG. 7, the laser microscope apparatus 40 according to this embodiment differs from the first embodiment in that it includes a detecting apparatus 41 formed by arranging a plurality of PPDs 17 in an array in directions intersecting the optical axis, and also includes, instead of the controller 19, a controller (adjusting mechanism) 43 that controls the driving of each PPD 17 in the detecting apparatus 41.

In the following, parts having the same configuration as those in the laser microscope apparatus 10 according to the first embodiment are assigned the same reference signs, and a description thereof is omitted.

In the detecting apparatus 41, the pixels in each of the PPDs 17 have the same size.

The controller 43 switches the driving voltage applied to each of the PPDs 17 on and off according to the beam diameter of the return light incident on the detecting apparatus 41.

For example, when using the objective lens 5 having the small exit NA, because the beam diameter of the return light after being converted to a substantially collimated beam by the collimator lens 15 is small, the controller 43 drives only the PPDs 17 in a required number of sections according to the beam diameter of the return light. In addition, when using the objective lens 5 having the large exit NA, because the beam diameter of the return light after being converted to a substantially collimated beam by the collimator lens 15 is large, the controller 43 drives all of the PPDs 17.

With the thus-configured laser microscope apparatus 40, by using the controller 43 to switch the PPDs 17 that are driven, according to the beam diameter of the return light, the effective detection area of the detecting apparatus 41 can be made substantially equal to the beam diameter of the return light, and it is possible to easily make photons uniformly incident on each pixel.

In this case, the PPDs 17 outside the beam diameter of the light incident on the pixels do not need to be driven. Therefore, by driving only the required PPDs 17 with the controller 43, dark noise can be reduced.

This embodiment can be modified in the following ways.

In this embodiment, although it has been assumed that the pixels of each PPD 17 have equal sizes, instead of this, for example, each PPD 17 may be formed so that the pixel sizes decrease the closer the pixels are disposed to the center portion of the effective detection area of the detecting apparatus 41, and may be formed so that the pixel sizes increase the closer the pixels are disposed to the edge portions of the effective detection area of the detecting apparatus 41.

The photon density of the return light incident on the detecting apparatus 41 differs at the optical axis center and edges, and photons tend to concentrate more closer to the optical axis center. Therefore, with this modification, the photons that concentrate at the optical axis center can be losslessly detected by the large number of small pixels disposed at the center portion of the effective detection area of the detecting apparatus 41, and thus, photon count loss can be reduced. In addition, the photons that are sparsely distributed at the optical axis edges can be detected by the small number of large pixels disposed at the edge portions of the effective detection area of the detecting apparatus 41, and thus, the aperture efficiency at the edge portions of the effective detection area can be improved.

Although the embodiments of the present invention have been described above with reference to the drawings, the specific configurations are not limited to these embodiments, and design modifications that do not depart from the scope of the present invention are also encompassed. For example, the present invention is not limited to one employed in the individual embodiments described above and may be employed in an embodiment formed by appropriately combining these embodiments, without particular limitation. In addition, in the second embodiment, the third embodiment, and the fourth embodiment, too, similarly to the second modification of the first embodiment, instead of using the confocal aperture 13, infrared pulsed laser light that induces two-photon excitation may be used as the excitation light, and the fluorescence generated by two-photon excitation may be detected.

REFERENCE SIGNS LIST

10, 20, 30, 40 laser microscope apparatus
14A, 14B, 14C optical system
15 collimator lens (adjusting mechanism)
16 collimator lens group
17 PPD (photodetector)
19, 23, 43 controller (adjusting mechanism)
21 uniform-illumination element (adjusting mechanism)
31 diverging element (adjusting mechanism)
33 internal-surface reflection element (adjusting mechanism)
41 detecting apparatus
S specimen

The invention claimed is:

1. A laser microscope apparatus comprising:
    an objective lens that collects light from a light source on a specimen and that collects the light from the specimen;
    a photodetector including a plurality of detection elements that detect the light collected by the objective lens, each of the plurality of detection elements being configured to detect only a single photon at the same time, the photodetector being configured to combine individual signals detected by the plurality of detection elements into one intensity signal and output the one intensity signal;
    an adjusting mechanism that makes a beam diameter of the light incident on the photodetector substantially equal to an effective detection area of the photodetector formed by the plurality of detection elements; and
    a scanning unit that two-dimensionally scans a focusing position on the specimen.

2. A laser microscope apparatus according to claim 1, wherein the adjusting mechanism adjusts the beam diameter according to an exit NA of the objective lens.

3. A laser microscope apparatus according to claim 2, wherein the adjusting mechanism includes:
    a collimator lens that converts the light collected by the objective lens into a substantially collimated beam; and a controller that moves the collimator lens to a prescribed position in an optical-axis direction, which is determined in advance according to the exit NA of the objective lens.

4. A laser microscope apparatus according to claim 2, wherein the adjusting mechanism includes:
a collimator lens group formed of a plurality of groups of optical systems, the collimator lens group converting the light collected by the objective lens into a substantially collimated beam; and
a controller that moves at least one of the groups of optical systems to a prescribed position in an optical-axis direction, which is determined in advance according to the exit NA of the objective lens.

5. A laser microscope apparatus according to claim 2, wherein the adjusting mechanism includes:
a collimator lens that converts the light collected by the objective lens into a substantially collimated beam;
a uniform-illumination element that is disposed, so as to be capable of moving in an optical-axis direction, between the collimator lens and the photodetector, and that causes the light converted to the substantially collimated beam by the collimator lens to diverge to form a substantially uniform intensity distribution; and
a controller that moves the uniform-illumination element to a prescribed position in the optical-axis direction, which is determined in advance according to the exit NA of the objective lens.

6. A laser microscope apparatus according to claim 3, wherein the prescribed position is determined in consideration of a wavelength dependency for the exit NA of the objective lens.

7. A laser microscope apparatus according to claim 4, wherein the prescribed position is determined in consideration of a wavelength dependency for the exit NA of the objective lens.

8. A laser microscope apparatus according to claim 5, wherein the prescribed position is determined in consideration of a wavelength dependency for the exit NA of the objective lens.

9. A laser microscope apparatus according to claim 1, wherein the adjusting mechanism includes:
a collimator lens that converts the light collected by the objective lens to a substantially collimated beam;
a diverging element that causes the light converted to the substantially collimated beam by the collimator lens to diverge; and
an internal-surface reflection element that reflects the light diverged by the diverging element at an internal surface thereof to converge inside the effective detection area of the photodetector.

10. A laser microscope apparatus according to claim 1, wherein the photodetector comprises a pixelated photon detector.

11. A laser microscope apparatus comprising:
an objective lens that collects light from a light source on a specimen and that collects the light from the specimen;
a photodetector including a plurality of detection elements that detect the light collected by the objective lens, each of the plurality of detection elements being configured to detect only a single photon at the same time;
an adjusting mechanism that makes a beam diameter of the light incident on the photodetector substantially equal to an effective detection area of the photodetector formed by the plurality of detection elements; and
a scanning unit that two-dimensionally scans a focusing position on the specimen,
wherein the adjusting mechanism adjusts the beam diameter according to an exit NA of the objective lens, and
wherein the adjusting mechanism includes:
a plurality of collimator lens groups, which have different spacings between optical systems in an optical-axis direction,
a switching mechanism configured to switch to a collimator lens group to be used among the plurality of the collimator lens groups, and
a controller that controls the switching mechanism so as to switch to a collimator lens group which is determined in advance according to the exit NA of the objective lens.

12. A laser microscope apparatus comprising:
an objective lens that collects light from a specimen;
a detecting apparatus in which a plurality of photodetectors are arranged in an array in directions intersecting an optical axis of light incident on the detecting apparatus, each of the photodetectors including a plurality of detection elements to detect the light collected by the objective lens; and
an adjusting mechanism that makes a beam diameter of the light incident on the detecting apparatus substantially equal to an effective detection area of the detecting apparatus, formed by the plurality of photodetectors, by switching the photodetectors to be driven according to the beam diameter of the light.

13. A laser microscope apparatus according to claim 12, wherein the adjusting mechanism drives the photodetectors which are determined in advance according to the exit NA of the objective lens.

14. A laser microscope apparatus according to claim 12, wherein each of the photodetectors is formed in such a manner that sizes of the detection elements become smaller the closer the detection elements are disposed to a center portion of the effective detection area of the detecting apparatus, and is formed in such a manner that the sizes of the detection elements become larger the closer the detection elements are disposed to edge portions of the effective detection area of the detecting apparatus.

15. A laser microscope apparatus according to claim 12, further comprising:
a scanning unit that two-dimensionally scans a focusing position on the specimen,
wherein the objective lens collects the light from a light source on the specimen, and
wherein, in each of the photodetectors of the detecting apparatus, each of the plurality of detection elements is configured to detect only a single photon at the same time.

16. A laser microscope apparatus comprising:
an objective lens that collects light from a light source on a specimen and that collects the light from the specimen;
a photodetector including a plurality of detection elements that detect the light collected by the objective lens, each of the plurality of detection elements being configured to detect only a single photon at the same time;
an adjusting mechanism that makes a beam diameter of the light incident on the photodetector substantially equal to an effective detection area of the photodetector formed by the plurality of detection elements; and
a scanning unit that two-dimensionally scans a focusing position on the specimen, wherein the adjusting mechanism adjusts the beam diameter according to an exit NA of the objective lens, and
wherein the adjusting mechanism includes:
- a collimator lens that converts the light collected by the objective lens into a substantially collimated beam; and
- a controller that moves the collimator lens to a prescribed position in an optical-axis direction, which is determined in advance according to the exit NA of the objective lens.

17. A laser microscope apparatus comprising:
an objective lens that collects light from a light source on a specimen and that collects the light from the specimen;
a photodetector including a plurality of detection elements that detect the light collected by the objective lens, each of the plurality of detection elements being configured to detect only a single photon at the same time;
an adjusting mechanism that makes a beam diameter of the light incident on the photodetector substantially equal to an effective detection area of the photodetector formed by the plurality of detection elements; and
a scanning unit that two-dimensionally scans a focusing position on the specimen,
wherein the adjusting mechanism adjusts the beam diameter according to an exit NA of the objective lens, and
wherein the adjusting mechanism includes:
- a collimator lens group formed of a plurality of groups of optical systems, the collimator lens group converting the light collected by the objective lens into a substantially collimated beam; and
- a controller that moves at least one of the groups of optical systems to a prescribed position in the optical-axis direction, which is determined in advance according to the exit NA of the objective lens.

18. A laser microscope apparatus comprising:
an objective lens that collects light from a specimen;
a photodetector including a plurality of detection elements that detect the light collected by the objective lens; and
an adjusting mechanism that makes a beam diameter of the light incident on the photodetector substantially equal to an effective detection area of the photodetector formed by the plurality of detection elements,
wherein the adjusting mechanism adjusts the beam diameter according to an exit NA of the objective lens, and
wherein the adjusting mechanism includes:
- a collimator lens that converts the light collected by the objective lens into a substantially collimated beam;
- a uniform-illumination element that is disposed, so as to be capable of moving in an optical-axis direction, between the collimator lens and the photodetector, and that causes the light converted to the substantially collimated beam by the collimator lens to diverge to form a substantially uniform intensity distribution; and
- a controller that moves the uniform-illumination element to a prescribed position in the optical-axis direction, which is determined in advance according to the exit NA of the objective lens.

19. A laser microscope apparatus according to claim 18, further comprising:
a scanning unit that two-dimensionally scans a focusing position on the specimen,
wherein the objective lens collects the light from a light source on the specimen, and
wherein each of the plurality of detection elements is configured to detect only a single photon at the same time.

20. A laser microscope apparatus comprising:
an objective lens that collects light from a light source on a specimen and that collects the light from the specimen;
a photodetector including a plurality of detection elements that detect the light collected by the objective lens, each of the plurality of detection elements being configured to detect only a single photon at the same time;
an adjusting mechanism that makes a beam diameter of the light incident on the photodetector substantially equal to an effective detection area of the photodetector formed by the plurality of detection elements; and
a scanning unit that two-dimensionally scans a focusing position on the specimen,
wherein the adjusting mechanism includes:
- a collimator lens that converts the light collected by the objective lens to a substantially collimated beam;
- a diverging element that causes the light converted to the substantially collimated beam by the collimator lens to diverge; and
- an internal-surface reflection element that reflects the light diverged by the diverging element at an internal surface thereof to converge inside the effective detection area of the photodetector.

* * * * *